United States Patent [19]

Hamada et al.

[11] 4,317,705
[45] Mar. 2, 1982

[54] METHOD FOR MEASURING CONCENTRATION OF OXIDANT OR REDUCTANT

[75] Inventors: Sumio Hamada; Kenji Usui; Takeshi Noguchi, all of Tokyo, Japan

[73] Assignee: Nissan Engineering Ltd., Tokyo, Japan

[21] Appl. No.: 222,625

[22] Filed: Jan. 5, 1981

Related U.S. Application Data

[62] Division of Ser. No. 112,289, Jan. 15, 1980, abandoned.

[30] Foreign Application Priority Data

May 28, 1979 [JP] Japan .................................. 54-65759

[51] Int. Cl.$^3$ ...................... G01N 27/46; G01N 27/52
[52] U.S. Cl. ................................... 204/1 T; 204/195 R
[58] Field of Search ........................... 204/1 T, 195 R

[56] References Cited

U.S. PATENT DOCUMENTS

| | | | |
|---|---|---|---|
| 3,503,861 | 3/1970 | Volpe | 204/195 P |
| 4,033,830 | 7/1977 | Fletcher | 204/1 T |
| 4,059,406 | 11/1977 | Fleet | 204/195 R X |
| 4,077,861 | 3/1978 | Lauer | 204/195 P |
| 4,166,775 | 9/1979 | Bruckenstein et al. | 204/1 T |
| 4,201,646 | 5/1980 | Matson | 204/195 R X |

FOREIGN PATENT DOCUMENTS

| | | | |
|---|---|---|---|
| 2736243 | 12/1978 | Fed. Rep. of Germany | 204/195 R |
| 1318189 | 5/1973 | United Kingdom | 204/195 R |

OTHER PUBLICATIONS

M. W. Breiter, J. Electrochem. Soc., vol. 112, No. 8, pp. 845-849, (1965).

Primary Examiner—G. L. Kaplan
Attorney, Agent, or Firm—Oblon, Fisher, Spivak, McClelland & Maier

[57] ABSTRACT

A method and an apparatus for automatic measurement of a concentration of an oxidant or a reductant comprises a solid electrode placed in an electrolytic cell in which a solution is flowed as a laminar flow;

a potentiostat for measuring said concentration of an oxidant or a reductant;

an electric potential sweeping device which is a continuous functional wave generator connecting to said potentiostat; and said continuous functional wave generator being used for washing said solid electrode by applying an alternating rectangular or pulse voltage having a frequency of 40 to 0.1 Hz.

The working solid disk electrode is cleaned by alternately oscillating a potential in a range of the anode and cathode potentials for causing an electrolysis of water.

1 Claim, 5 Drawing Figures

METHOD FOR MEASURING CONCENTRATION OF OXIDANT OR REDUCTANT

This is a division of application Ser. No. 112,289, filed Jan. 15, 1980 and now abandoned.

BACKGROUND OF THE INVENTION

1. Field of the Invention

The present invention relates to a method and an apparatus for continuously measuring a concentration of an oxidant or a reductant in a process fluid in a chemical plant, etc. by utilizing dependency of currents for concentrations in an electrolytic oxidation or reduction of the oxidant or reductant on a working solid electrode made of gold, platinum, carbon-paste etc.

2. Description of Prior Arts

A concentration of an oxidant or a reductant has been measured by various methods. A potentiostat has been used for the measurement of a concentration of an oxidant and a reductant. However, the continuous measurement of the concentration of an oxidant or a reductant has not been satisfactorily achieved.

An electrochemical measurement for analyzing current-potential characteristics by applying a voltage to a working solid electrode set in a fluid has been known as a hydrodynamic voltammetry. The current-potential characteristic curves obtained by the hydrodynamic voltammetry are similar to those of polarography used in various fields. However, waves obtained in a laminar flow control have not the current oscillation caused by using a dropping mercury electrode, and height of the limiting diffusion current in the current-potential characteristic curve is usually high. A height of a limiting diffusion current is proportional to a concentration of an oxidant or a reductant in a solution and is used for a quantative analysis.

When the wave is a reduction wave in a simple oxidation-reduction system

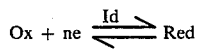

wherein Ox: oxidant; e: electron; and Red: reductant, the relation of

Id α Cox wherein Id: limiting diffusion current; and Cox: concentration of oxidant, is given in both of the polarography and the hydrodynamic voltammetry. The limiting diffusion current Id can be also shown by the equation:

Id = K·F·Cox wherein K: constant; and F: function given by flowing condition.

The hydrodynamic voltammetry is mainly classified into two methods.

In one method, an electrode is moved in a solution in the stationary condition. The typical one is to use a rotating disk electrode.

In the other method, a solution is forcibly flowed toward an electrode in the stationary condition. The former has been mainly studied. However, the former method has disadvantages that a mechanical sliding part is needed as an electric contact for the rotating disk electrode, and a synchronous motor having no fluctuation of rotary speed is needed in the continuous measurement of a concentration of an oxidant or a reductant in an industrial process fluid, and the maintenance is not easy in view of anticorrosive and durable property.

SUMMARY OF THE INVENTION

It is an object of the present invention to provide a method and an apparatus for continuously measuring a concentration of an oxidant or a reductant.

The foregoing and other objects of the present invention have been attained by providing an apparatus for automatic measurement of a concentration of an oxidant or a reductant which comprises a solid electrode placed in an electrolytic cell in which a solution is flowed as a laminar flow; a potentiostat for measuring said concentration of an oxidant or a reductant;
an electric potential sweeping device which is a continuous functional wave generator connecting to said potentiostat; and
said continuous functional wave generator being used for washing said solid electrode by applying an alternating rectangular or pulse voltage having a frequency of 40 to 0.1 Hz.

DETAILED DESCRIPTION OF THE PREFERRED EMBODIMENTS

The hydrodynamic voltammetry setting a stationary electrode in a fluid is suitable for measuring a concentration of an oxidant or a reductant, especially to control a concentration of sodium hypochlorite, in comparison with the hydrodynamic voltammetry using a rotating disk electrode in view of the simple structure and no requirement of a motor.

Figure 2:
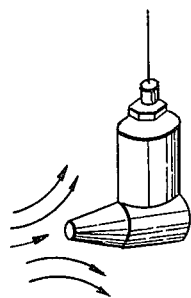
FIG. 2 is a schematic view of an electrode wherein stream lines near a platinum electrode are shown.

An electrolytic system having a stagnation point electrode shown in FIG. 2 is suitable for the hydrodynamic voltammetry in which a solution is forcibly flowed toward a stationary electrode.

The electrode has a structure that a solid disk electrode is buried in a shell shaped capsule which can have stream line shape or like so as to give the laminar flow of the solution.

The electrolytic system will be further described.

In one example, the electrolytic system comprises an electrolytic cell body made of a resin such as polyvinyl chloride which has a diameter of 100 mm. and a height of 90 mm.; and a working electrode and a reference electrode and a counter electrode. An inlet for the solution is formed on a side surface of the electrolytic cell and an outlet for the solution is formed on the rear surface of the electrolytic cell. The level of the solution in the inlet side is kept constant so as to maintain the constant flow rate of the solution. The working electrode is prepared by combining a cylinder made of a resin such as polyvinyl chloride having a height of 50 mm. and a diameter of 30 mm. with a shell shaped body made of a resin such as polyvinyl chloride having a length of 60 mm. and a diameter of 20 mm. and a platinum electrode having a diameter of 4 mm. which is buried at the top of the shell shaped body. The surfaces of the electrode and the shell shaped body have curvatures of $6^R$ at the top and $50^R$ at the side surface so as to maintain the laminar flow. The counter electrode and the reference electrode are set at the rear side of the working electrode so as to prevent disturbing of stream lines near the working electrode. Certain potential is always applied to the electrodes by the potentiostat.

In order to prevent a surface shield of the stationary electrode in micro which is caused by physical contamination or adsorbed ions, a function generator which emits a continuous triangular electric signal or a continuous rectangular electric signal as a circuit for cleaning the working electrode, is used.

In the operation for the measurement, the potential of the working solid electrode is alternately oscillated in suitable period in a range of the anode and cathode potentials for causing an electrolysis of water. The contamination adsorbed on the surface of the electrode is removed by washing it with fine bubbles resulting on the surface of the electrode by the electrolysis of water. The adsorbed ions are also removed from the surface of the electrode by alternately oscillating the potential between the anode and cathode potentials. Accordingly, the reproducibility in the measurement of the limiting diffusion current by the potentiostat at the set potential is remarkably improved and the concentration of an oxidant or a reductant can be measured in high accuracy.

The absolute potential of the electrode in the oscillation (vs.Ag/AgCl(3M-KCl)) is higher than the absolute potential in an electrolysis of water. The minimum potential of the electrode in the oscillation is usually $-1.0$ to $-5.0$ volt and/or the maximum potential of the electrode in the oscillation is usually $+0.5$ to $+5$ volt.

EXAMPLE

Figure 1:
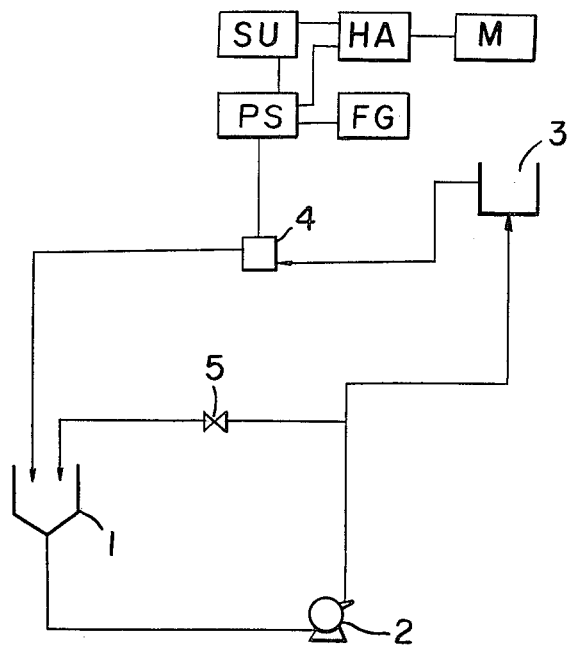
FIG. 1 is a flow diagram of a test apparatus using a process analyzer of the present invention.

An apparatus equipped with a polarographic analyzer which is shown in FIG. 1 was used.

Each alkaline aqueous solution of sodium hypochlorite (pH=10) (KCl: 1 mol/l) as a sample was fed from a recycle vessel (1) through a recycle pump (2) to a degasification vessel (3). The aqueous solution was further fed from the degasification (3) to an electrolytic cell (4), in level difference and was returned to the recycle vessel (1). A temperature of the aqueous solution was measured by a thermometer placed in the electrolytic cell. A flow rate was measured by a messcylinder and a stopwatch. The flow rate was controlled by a flow rate controlling valve (5). An electric potential sweeping was applied to the working electrode potentiostat PS by functional wave generator FG. Limiting diffusion currents were measured by an output ampere meter M at $-0.5$ V (vs. Ag/AgCl (3M-KCl)). SU is a sequence unit which has a timer for switching the measurement and the regeneration of the electrode. HA is a hold amplifier which is used for displaying the measured current even when the measurement is stopped for changing the potential. The voltage applied to the electrodes was varied for several times to the cathode direction and to the anode direction for the purpose of the electrode cleaning before the measurement. The resulting data were collected.

Figure 3:
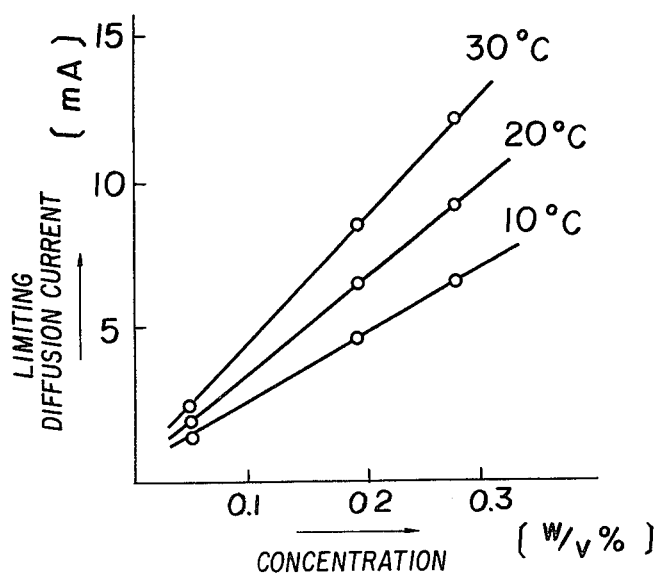
FIGS. 3, 4 and 5 are graphs of diffusion currents depending upon concentrations, temperatures and flow rates.

In FIG. 3, the detected currents to the concentrations were plotted as parameters of the temperatures.

Figure 4:
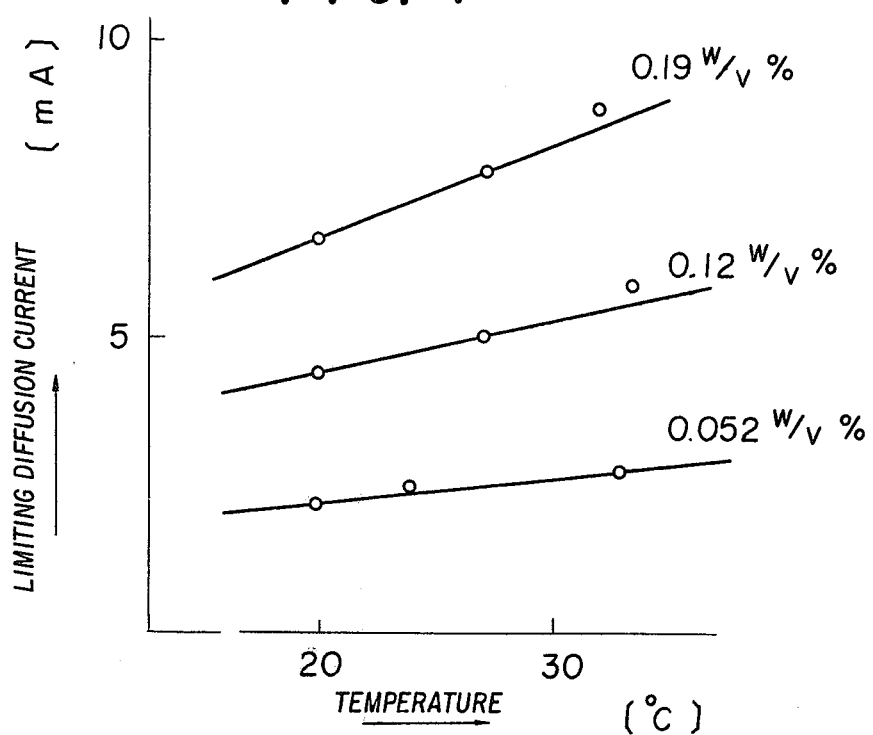

In FIG. 4, the detected currents to the temperatures were plotted as parameters of the concentrations.

Figure 5:
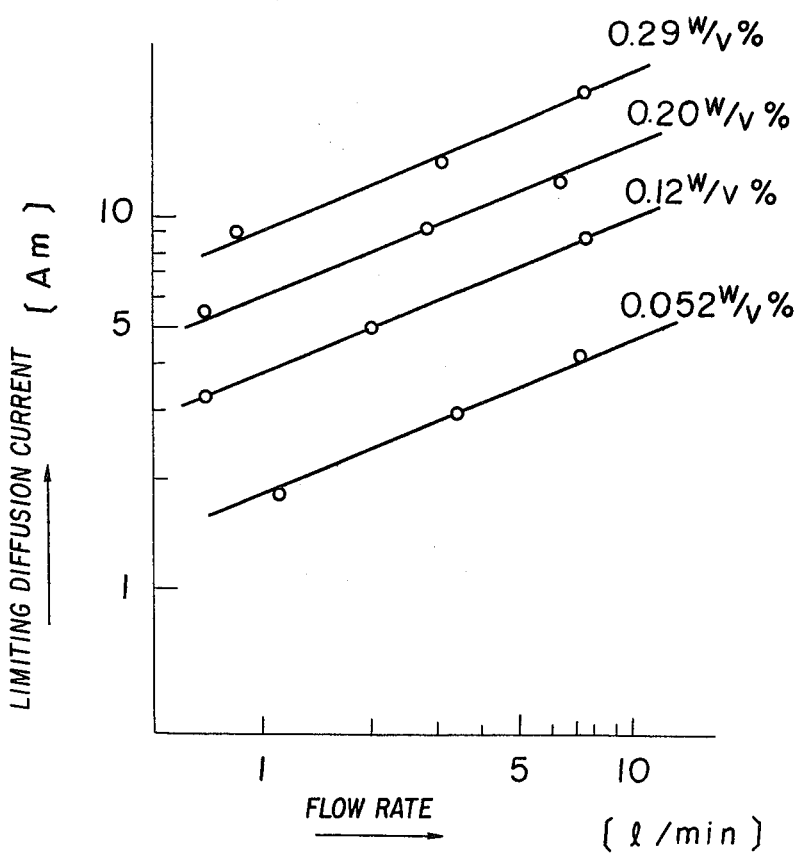

In FIG. 5, the detected currents to the flow rates were plotted as parameters of the concentrations.

In FIGS. 3 to 5, excellent linearities were found. This fact shows that the concentration can be detected by the current value.

In the above-mentioned tests, reduction waves for $ClO^-$ in an alkaline aqueous solution were measured.

When a polarogram can be obtained by a working electrode made of platinum, gold, etc. in an oxidation-reduction system, a concentration of any material can be measured. For example, the oxidation-reduction systems of $Fe(CN)_6^{3-}/Fe(CN)_6^{4-}$; quinone/hydroquinone; $I^-/I_2$; Fe(II)EDTA/Fe(III)EDTA etc. can be used.

The apparatus shown in FIG. 1 was used for measuring each concentration of each compound shown in the following table under the conditions shown in the table, the measurements in all of the cases could be continued for longer than 24 hours.

| Note: | | |
|---|---|---|
| | neu. | : neutral |
| | tri. pulse | : triangular pulse |
| | rect. pulse | : rectangular pulse |

TABLE

| Compound | Potential** in measurement (Volt) | Potential in oscillation as pretreatment (Volt) | | Waveform in oscillation | Concentration solution | Reproducible Time (Hour) |
|---|---|---|---|---|---|---|
| $OCl^-$ | $-0.5$ | $+0.5$ | $-3.0$ | tri. pulse | 1mM,1 MKCl NaOH pH = 10 | 24< |
| $Fe(CN)_6^{3-}$ | $-0.4$ | $+0.5$ | $-2.0$ | tri. pulse | 0.5mM 1 MKCl neu. | 24< |
| $Fe(CN)_6^{4-}$ | $+0.3$ | $+0.5$ | $-2.0$ | tri. pulse | 0.5mM 1 MKCl neu. | 24< |
| $I_2^-$ | $-0.5$ | $+0.5$ | $-3.0$ | tri. pulse | 0.1mM 1 MNaCl neu. | 24< |
| quinone | $-0.7$ | $+0.1$ | $-3.0$ | rect. pulse | 1mM 1 MKCl neu. | 24< |
| hydroquinone | $+0.5$ | $+0.5$ | $-2.0$ | rect. pulse | 1mM 1 MKCl neu. | 24< |
| Naphthoquinone sodium sulphate | $-0.9$ | $-0.5$ | $-3.0$ | tri. pulse | 1mM 1 MNa$_2$CO$_3$ pH = 12 | 24< |
| Naphthohydroquinone sodium sulphate | $+0.5$ | $+0.5$ | $-2.0$ | tri. pulse | 1mM 1 MNa$_2$CO$_3$ pH = 12 | 24< |
| Fe(II)-EDTA | $+0.5$ | $+0.5$ | $-2.5$ | rect. pulse | 1mM HCl pH = 3 | 24< |
| Fe(III)-EDTA | $-0.3$ | $+0.5$ | $-2.0$ | rect. pulse | 1mM HCl pH = 3 | 24< |
| Anthraquinone | $-0.8$ | $+0.1$ | $-2.5$ | tri. pulse | 0.1mM acetate 40% dioxane | 24< |
| p-toluquinone | $-0.5$ | $-0.3$ | $-3.0$ | tri. pulse | phosphate 70% ethanol | 24< |
| o-benzoquinone | $-0.3$ | $-0.3$ | $-2.0$ | rect. pulse | 0.2mM buffer solution pH = 5 | 24< |
| o-dinitrobenzene | $-0.6$ | $-0.2$ | $-2.0$ | tri. pulse | 1mM buffer solution | 24< |

TABLE-continued

| Compound | Potential** in measurement (Volt) | Potential in oscillation as pre-treatment (Volt) | Waveform in oscillation | Concentration solution | Reproducible Time (Hour) |
| --- | --- | --- | --- | --- | --- |
| m-dinitrobenzene | −0.5 | −0.2 −2.0 | tri. pulse | 10% ethanol pH = 7 1mM buffer solution | 24< |
| p-dinitrobenzene | −0.5 | −0.2 −2.0 | tri. pulse | 8% ethanol pH = 7 1mM buffer solution | 24< |
| o-nitrotoluene | −0.6 | −0.5 −2.5 | tri. pulse | 8% ethanol pH = 7 0.5mM buffer solution | 24< |
| m-nitrotoluene | −0.8 | −0.5 −2.5 | tri. pulse | 80% dioxane pH = 1 1mM buffer solution | 24< |
| p-nitrotoluene | −0.9 | −0.5 −2.5 | tri. pulse | 80% dioxane pH = 1.0 1mM buffer solution | 24< |

TABLE-continued

| Compound | Potential** in measurement (Volt) | Potential in oscillation as pre-treatment (Volt) | Waveform in oscillation | Concentration solution | Reproducible Time (Hour) |
| --- | --- | --- | --- | --- | --- |
| $O_2$ | −0.5 | −0.5 −2.0 | tri. pulse | 80% dioxane pH = 1.0 0.1mM 0.1 M NaOH | 24< |
| $Br_2$ | −0.4 | −0.4 −2.0 | rect. pulse | 1mM 1 MNaCl | 24< |
| $Br^-$ | +0.5 | +0.5 −2.0 | rect. pulse | 1mM 1 MNaCl | 24< |

**vs. Ag/Ag Cl (3M KCl)

We claim:

1. A method of continuously measuring the concentration of an oxidant or reductant which comprises flowing in an electrolytic cell as a laminar flow a solution containing an oxidant or reductant, measuring the concentration of said oxidant or reductant by means of a potentiostat to which is connected an electric potential sweeping device which is a continuous functional wave generator, and effecting said measurement of the concentration while applying to the solution in the electrolytic cell an alternating rectangular or pulse voltage having a frequency of 40 to 0.1 Hz. wherein the alternations oscillate between a first voltage which is an applied negative potential higher than the electrolysis potential of water, and a second voltage which is an applied positive potential, whereby said first voltage effects contamination removal and said second voltage effects adsorbed ion removal from the electrode surface.

* * * * *